United States Patent [19]
Kobayashi

[11] Patent Number: 5,451,319
[45] Date of Patent: * Sep. 19, 1995

[54] ANAEROBIC DIGESTION PROCESS FOR SEWAGE SLUDGE

[76] Inventor: Yoshio Kobayashi, 543-10 Shichiyama, Kumatori-cho, Sennan-gun, Osaka, Japan

[*] Notice: The portion of the term of this patent subsequent to Mar. 1, 2011 has been disclaimed.

[21] Appl. No.: 202,656

[22] Filed: Feb. 28, 1994

Related U.S. Application Data

[63] Continuation-in-part of Ser. No. 596,917, Oct. 15, 1990, Pat. No. 5,290,450, which is a continuation-in-part of Ser. No. 330,256, Mar. 29, 1989, abandoned.

[30] Foreign Application Priority Data

Mar. 30, 1988 [JP] Japan .................. 63-74606

[51] Int. Cl.⁶ .......................... C02F 3/28
[52] U.S. Cl. .................. 210/603; 210/609; 210/613
[58] Field of Search ............. 210/603, 609, 613, 615, 210/631

[56] References Cited

U.S. PATENT DOCUMENTS

| | | | |
|---|---|---|---|
| 3,402,103 | 9/1968 | Amberg et al. | 210/615 |
| 3,959,125 | 5/1976 | Teletzke | 210/603 |
| 3,981,800 | 9/1976 | Ort | 210/609 |
| 4,040,953 | 8/1977 | Ort | 210/609 |
| 4,088,571 | 5/1978 | Helgesson | 210/615 |
| 4,132,638 | 1/1979 | Carleson | 210/609 |
| 4,342,836 | 8/1982 | Harvey | 210/603 |
| 4,388,186 | 6/1983 | Fujimoto et al. | 210/603 |
| 4,396,402 | 8/1983 | Ghosh | 210/613 |
| 4,400,195 | 8/1983 | Rijkens | 210/603 |
| 4,684,468 | 8/1987 | DeBaere | 210/613 |

FOREIGN PATENT DOCUMENTS

| | | |
|---|---|---|
| 225983 | 8/1985 | Germany . |
| 60-48198 | 3/1985 | Japan . |
| 61-230797 | 10/1986 | Japan . |
| 1037683 | 8/1966 | United Kingdom . |
| 1110352 | 4/1968 | United Kingdom . |
| 2047223 | 11/1980 | United Kingdom . |
| 8501281 | 3/1985 | WIPO . |

OTHER PUBLICATIONS

*Webster's Third New International Dictionary of the English Language*, p. 218 (1971).
*Biotechnology Encyclopedia*, p. 625 (1986).
*Methane Production from Agricultural and Domestic Wastes*, Hobson et al., Applied Science Publishers, Ltd., London (1981), pp. ix–xi.

Primary Examiner—Christopher Upton
Attorney, Agent, or Firm—Lowe, Price, LeBlanc & Becker

[57] ABSTRACT

An anaerobic digestion process for sewage sludge comprises the steps of dewatering raw sewage sludge to provide a solids content therein in the range of 10 to 25 weight %, recirculating a portion of digested sludge resulting from methane fermentation and having a dry solids content lower than that of said dewatered raw sewage sludge, adding one part by weight of the dewatered raw sewage sludge to at least one part by weight of the recirculated digested sludge, homogeneously kneading the resulting mixture for inoculation, and causing methane fermentation of the inoculated sludge mixture in a tube-shaped digestor. The inoculated sludge is moved in the longitudinal direction of the tube in the digestor during methane fermentation, and a portion of the sludge discharged from the digestor is recirculated.

5 Claims, 8 Drawing Sheets

ANAEROBIC DIGESTION PROCESS FOR SEWAGE SLUDGE

RELATED APPLICATION

The present application is a continuation-in-part of application Ser. No. 07/596,917 filed Oct. 15, 1990, now U.S. Pat. No. 5,290,450 which is a continuation-in-part of application Ser. No. 07/330,256 filed Mar. 29, 1989, now abandoned.

FIELD OF THE INVENTION

The present invention relates to an anaerobic digestion process for sewage sludge.

BACKGROUND OF THE INVENTION

In general, sludge is discharged from a sewage-treatment plant in a state having a solids content of about 2 weight %. In a conventional method for reducing the amount of such discharge, the sludge is guided to a digestor chamber for methane fermentation.

In such a conventional method, however, a digestor chamber having a large capacity is required since the rate of fermentation is slow and the sludge concentration is very dilute. Further, the conventional method is inferior in economic efficiency since the sewage gas yield thereof is 40 to 50%, at most, with the result that a considerable part of the sewage gas generated through digestion is employed in heating the sludge.

In improving sludge digestion techniques, a first important goal is to reduce the size of the digestor chamber, and a second goal is to improve the heat balance, as well as the sewage gas generation efficiency, in the process. An attempt has recently been made to enrich the sludge for increasing its solids content from about 2 weight % to 4 to 6 weight %, in order to reduce the capacity of the digestor chamber and to improve the heat balance so as to be able to recover energy through a sewage gas power generation system. However, sufficient economic efficiency cannot yet be obtained through such enrichment, and further improved performance is desired.

Two methods are generally known for improving the efficiency of methane fermentation. The first method is generally referred to as "thermophilic digestion" wherein the methane fermentation is performed at a relatively high temperature greater than about 50° C., i.e., in the range of from 50° C. to 55° C. The fermentation temperature can be as high as about 65° C., although higher temperatures are avoided in order to prevent destruction of the inoculant which is employed for methane fermentation. The thermophilic digestion method is disclosed by Hobson et al, *Methane Production From Agricultural and Domestic Wastes*, Applied Science Publishers, Ltd. (1981), pages 190, 226–228. In the thermophilic digestion method, the speed of fermentation is increased from 2 to 2.5 times that in ordinary methane fermentation conducted at a temperature of, for example, 35° C.

The second of the generally known methods for improving the efficiency of methane fermentation is referred to as "thermal pretreatment" wherein heat treatment of raw sludge is performed prior to methane fermentation. The thermal pretreatment provides increased efficiency in methane fermentation by converting organic substances which are not easily decomposed into more biodegradable organic forms. The thermal pretreatment involves heating the raw sludge to temperatures greater than about 50° C., and often temperatures in the range of from about 60° C. to about 180° C. are employed. Thermal pretreatment methods are disclosed by Hobson et al at page 188, Haug et al, "Effect of Thermal Pretreatment on Digestibility and Dewaterability of Organic Sludges," *Journal of Water Pollution Control Federation*, 50 (1), January 1978, pages 73–85, and Hiraoki et al, "Highly Efficient Anaerobic Digestion With Thermal Pretreatment," *Water Science and Technology*, Volume 17, Amsterdam (1984), pages 529–539. For example, Haug et al disclose that methane production increases 14% with the use of a thermal pretreatment at 100° C. and 60 to 70% with a thermal treatment conducted at 175° C. Hiraoki et al also disclose that gas production yield increases more than 30% with the use of a thermal pretreatment at a temperature of from 60° to 80° C.

Thus, the thermophilic digestion and thermal pretreatment methods are effective in improving the efficiency of sludge digestion. However, if the concentration of the sludge is from about 4 to 6%, the heating temperature is limited to about 30° C. since excessively large quantities of heat are required for further heating. Thus, methane fermentation cannot be advantageously conducted at a temperature of 50° to 55° C. as required in the thermophilic digestion and raw sludge cannot be advantageously heated to temperatures greater than 50° C. as required in the thermal pretreatment method in ordinary sewage treatment plants since excessively large quantities of heat are required for such treatments.

SUMMARY OF THE INVENTION

Accordingly, it is an object of the present invention to provide an anaerobic digestion process for sewage sludge, which process improves the generation efficiency of sewage gas while reducing the capacity of the digestor chamber.

The present invention provides a sewage sludge anaerobic digestion process wherein a portion of digested sludge resulting from methane fermentation is recirculated and raw sludge is added to the recirculated portion of the digested sludge to cause methane fermentation. According to the present invention, the anaerobic digestion process for sewage sludge includes the steps of dewatering raw sewage sludge to provide a solids content therein in the range of from 10 to 25 weight %; recirculating a portion of digested sludge resulting from methane fermentation and having a lower solids content than the dewatered raw sewage sludge; adding one weight part of the dewatered raw sewage sludge to at least one weight part of the recirculated digested sludge; homogeneously kneading the resulting mixture for inoculation; and causing methane fermentation of the inoculated sewage sludge in a tube shaped digestor. The inoculated sludge is moved in the longitudinal direction of the tube in the digestor during methane fermentation and a portion of the sewage sludge discharged from the digestor is recirculated as the mixture moves.

Generally, a raw sewage sludge is discharged from a sewage treatment plant in a state having a solids content of about 2 to 5 weight % for methane fermentation. In the present invention, the raw sewage sludge is dewatered to have a solids content in the range of 10 to 25 weight % and preferable in the range of 10 to 21 weight %. Dewatering may be effected by conventional dewatering methods, such as centrifugal dewater, belt press dewater, pressure dewater and vacuum dewater. The raw sewage sludge rapidly attains a high viscosity as its water content decreases. The higher the viscosity, the more difficult the common stirring operation becomes. If the rate of dewatering is too high, it is inconvenient in view of transportation, stirring, and in $NH_3$ concentration, which will be described later. From these points, the preferable range of the solids content of the dewatered raw sewage sludge is from 10 to 25 weight %.

In addition, the sewage sludge has a higher N content and a lower C/N (Carbon content/Nitrogen content) ratio of, for example, 6 to 10 as compared with household waste and agricultural waste such as beet waste, potato waste, vegetable waste, straw and alcohol distillation waste. Nitrogenous substances in the raw sewage sludge which is made dense by dewatering are converted to $NH_3$ of high concentration by methane fermentation, and this $NH_3$ of high concentration inactivates microbes contributing toward methane fermentation. The content of nitrogenous substances in the household waste and agricultural waste such as beet waste, potato waste, vegetable waste, straw and alcohol distillation waste is lower than about one fourth of the sewage sludge, and the C/N ratio thereof is about four times higher. If household or agricultural waste is subjected to methane fermentation with high solids concentration of about 20 weight % or more, the concentration of $NH_3$ generated from the nitrogenous substance does not cause any substantial damage to the microbes but rather brings about a preferable value for fermentation.

Methane fermentation of the agricultural waste and household waste has been effected with a solids content as high as from 10 to 20%, while the concentration limit for methane fermentation of sewage sludge has been assumed to be 8% according to the prior art. This may be derived from the difference in chemical composition as described above as well as from restrictions caused by the highly viscose physical property. Manner and condition for methane fermentation differ depending on the chemical and physical properties of the substrate. However, based on such background the inventor has found that the concentration of sewage sludge preventing methane fermentation from a chemical aspect, for example ammonia concentration, is not lower than 8 weight %. based on this finding, a process for methane fermentation which is highly energy-effective could be implemented by subjecting raw sewage sludge dewatered to have a solids content considerably higher than the common solids content as present mixed homogeneously with digested sewage sludge. In addition, the inventor has found that stirring, which has been effected in conventional methane fermentation, is not necessary provided that the seeding is sufficiently homogeneous. Based on this knowledge, methane fermentation of a type in which seeded sewage sludge is transferred by plug flow without stirring the sludge in a tube-shaped digester chamber could be implemented. Especially, this process eliminated the restriction of high viscosity on methane fermentation, and enabled methane fermentation at high concentration exceeding the prior art upper limit of 8%. Taking into consideration that the concentration of nitrogen components in sewage sludge is relatively high, there is naturally an upper limit of the solids content of the raw sewage sludge to be subjected to methane fermentation. Preferably, the solids content of the dewatered raw sewage sludge should, therefore not exceed 25 weight %.

The dewatered raw sewage sludge is mixed with recirculated digested sludge for seeding. The solids content of the digested sludge decreases by the amount of organic substances converted to gas by digestion of raw sewage sludge. In other words, the content of sewage sludge contained in the digestor chamber is relatively lower than the solids content of the raw sewage sludge which is supplied. Preferably, the digested sludge should have the solids content of at most 15 weight %. With the solids contents within this range, it is sufficiently fluent for fermentation operation such as seeding and transportation. Digested sludge of more than 1 part by weight is added to 1 part by weight dewatered raw sewage sludge to be mixed, and the solids content of the seeded raw sewage sludge obtained by mixing becomes smaller than that of the dewatered raw sewage sludge. By this seeding, a sufficient amount of microbes for methane fermentation is applied to the substrate of the raw sewage sludge. If the ratio of mixture is lower than 1, it will incur overload to the microbes, which makes sufficient fermentation difficult. In order to bring the microbes into sufficient contact with the raw sewage sludge, the sludge mixture is homogeneously kneaded. For homogeneous seeding, it is necessary that kneading is effected not in the digester chamber but at a separate place.

In the present invention, the raw sewage sludge may preferably be heat-treated at a temperature in the range of about 60° to about 180° C. prior to the step of addition. Methane fermentation may preferably be effected at a temperature of about 50° C. or higher.

The present invention is also applicable to a so-called two-phase anaerobic digestion process in which the methane fermentation step is separated into an acid formation step and a methanation step. In this case, raw sludge is dewatered to provide a solids content of 10 to 25 weight %, and the dewatered sludge is added to a portion of digested sludge resulting from acid formation fermentation. The resulting mixture is homogeneously kneaded. The kneaded sludge is subjected to acid formation fermentation, and products of acid formation fermentation are guided to a methanation chamber to generate methane. Preferably, the products of acid formation fermentation are separated in the form of a filtrate, by filtering the digested sludge after acid formation fermentation. The products of acid formation fermentation contained in the obtained filtrate are subjected to methanation fermentation by contact with a fixed biocatalyst in the methanation chamber. The term "acid formation fermentation" indicates fermentation generating lower fatty acids, alcohols and carbon dioxide gas, etc., from organic substances contained in the sludge.

In the two-phase anaerobic digestion process, improved efficiency can be obtained by heating the dewatered raw sludge and/or fermenting at a relatively high temperature as discussed above. According to such a two-phase anaerobic digestion process, kneading high-viscosity raw sludge and seed sludge becomes easier and an even higher efficiency can be achieved.

According to the present invention, the digestor chamber can be reduced in capacity as compared with the conventional art, since raw sludge is dewatered to a solids content of 10 to 25 weight %. If the capacity of the digestor chamber is similar to that in the conventional art, a larger amount of raw sludge can be digested.

According to the present invention, the amount of water in the raw sludge to be heated is reduced as compared with the conventional art since the sludge has a high solids content. Therefore, according to the present invention, it is possible to perform the heat treatment of raw sludge and the high-temperature fermentation which have not been previously practical.

A sewage-treatment plant may be provided with equipment for sewage gas power generation. According to the present invention, sludge can be heated through exhaust heat generated in the power generation system. Thus, the present invention is particularly suitable for such a treatment plant.

These and other objects, features, aspects and advantages of the present invention will become more apparent from the following detailed description of the present invention when taken in conjunction with the accompanying drawings.

DETAILED DESCRIPTION

The process of the present invention and the improvements thereof are illustrated by the following examples and reference examples.

FILL AND DRAW METHOD EXPERIMENT

The present invention has been studied through a Fill and Draw method experiment.

Seed sludge was prepared by dewatering a sludge digested at 50° to 55° C. into a solids content of 15%. Raw sludge was dewatered to a solids content of 21%. Heat-treated sludge was prepared by heating the dewatered raw sludge at about 170° C. for 30 minutes.

EXAMPLE 1

Figure 1:
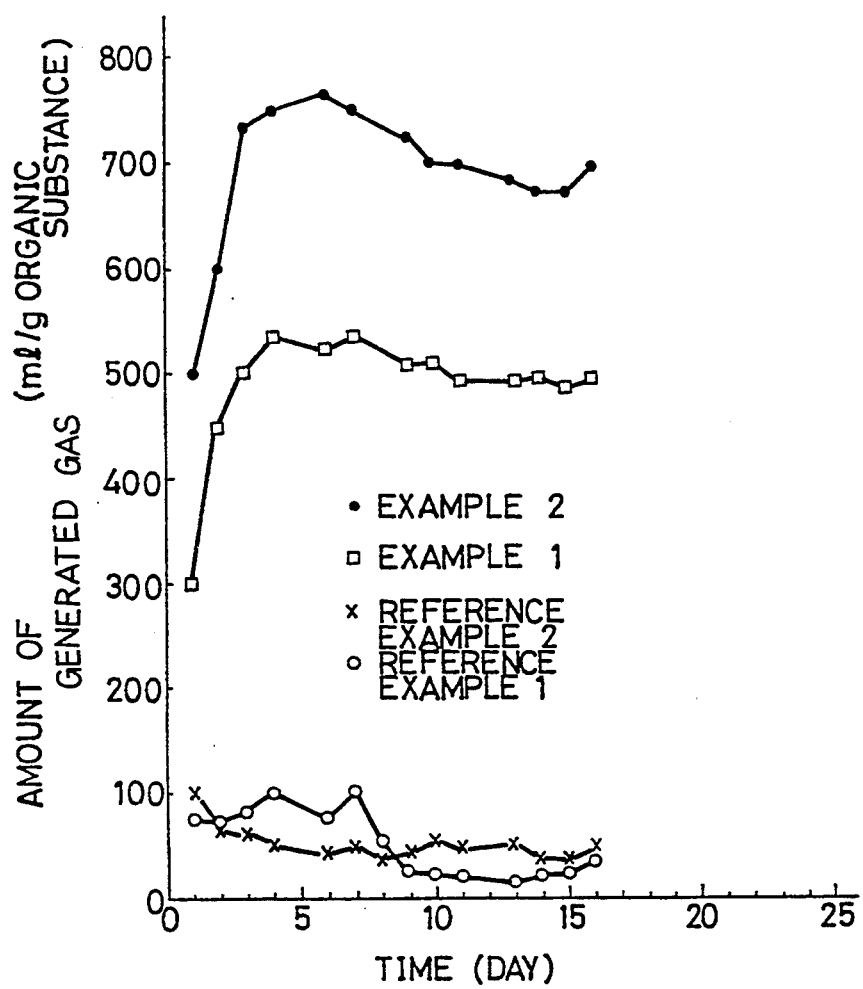
FIG. 1 illustrates the amounts of gas generated in a Fill and Draw method experiment.
Figure 2:
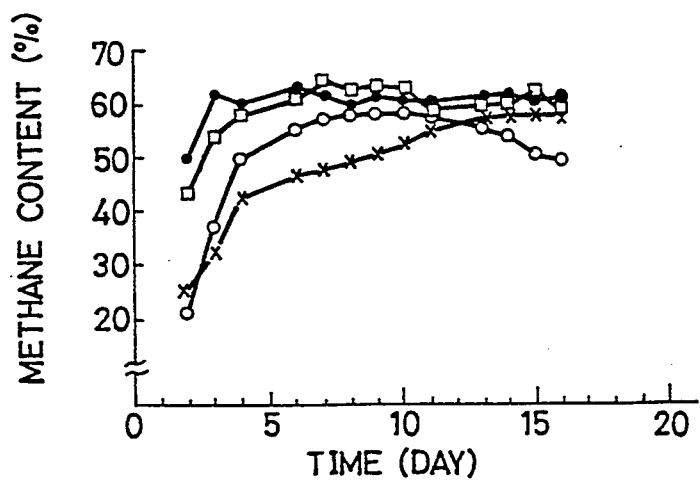
FIG. 2 illustrates methane contents in the gas generated in the Fill and Draw method experiment.

Seed sludge (200 g) and raw sludge (2.6 g) were introduced into a hermetically sealed laboratory kneader having an approximate content volume of about 1000 ml and an exhaust port, and substitution was performed in a pot of the kneader by nitrogen gas. Kneading was then performed for five minutes and thereafter the kneader was dipped and maintained in a constant-temperature water bath of 53° C. Digested gas thus generated was collected in a scavenging bottle, and the amount of generated gas and the methane content were measured the following day. Then, 2.6 g of the sludge was extracted from the pot of the kneader, and 2.6 g raw sludge was newly added and kneaded for five minutes. This operation was performed once a day, and this experiment was continued for 16 days. FIG. 1 shows the amount of generated gas and FIG. 2 shows the methane content of the generated gas.

Reference Example 1

Seed sludge (200 g) and raw sludge (2.6 g) were introduced into a 300 ml conical flask, and stirred and mixed by a glass rod with substitution in the flask with nitrogen gas. The conical flask was covered with a rubber stopper provided with a digested gas extraction port, and then maintained in a constant temperature bath of 53° C. Digested gas thus generated was collected in a scavenging bottle, and the methane content was measured on the next day. Then, 2.6 g of the sludge was extracted from the flask, and 2.6 g raw sludge was newly added and stirred and mixed by the glass rod. This operation was performed once a day, and this experiment was continued for 16 days. FIGS. 1 and 2 show the results thus obtained.

EXAMPLE 2

The raw sludge employed in Example 1 was replaced by heat-treated sludge. The amount of generated gas and the methane content in the generated gas were measured in a manner similar to Example 1. FIGS. 1 and 2 show the results.

Reference Example 2

The raw sludge employed in Reference Example 1 was replaced by heat-treated sludge, which was mixed into seed sludge and digested similarly to Reference Example 1, followed by measurement of the amount of generated gas and the methane content. FIGS. 1 and 2 show the results thus obtained.

As shown in FIG. 1, the amount of gas generated in Example 1, in which the sludge was sufficiently mixed in the laboratory kneader, was significantly higher than that of Reference Example 1, in which stirring was insufficient. The amount of generated gas is indicated in ml per g of organic substance contained in the sludge. The amount of gas generated in Reference Example 1 was at a level substantially identical to that obtained in conventional digestion performed in low concentration.

In Example 2, the raw sludge was heat-treated in advance. As shown in FIG. 1, the amount of gas generated in Example 2 was higher than that in Example 1. Thus, it is understood that the sewage gas yield was improved by the heat treatment, resulting in generation of a large amount of gas. Further, it is understood that the sludge must be sufficiently mixed also, from a comparison of Example 2 with Reference Example 2 employing the heat-treated-sludge.

Bench Scale Experiment

Figure 3:
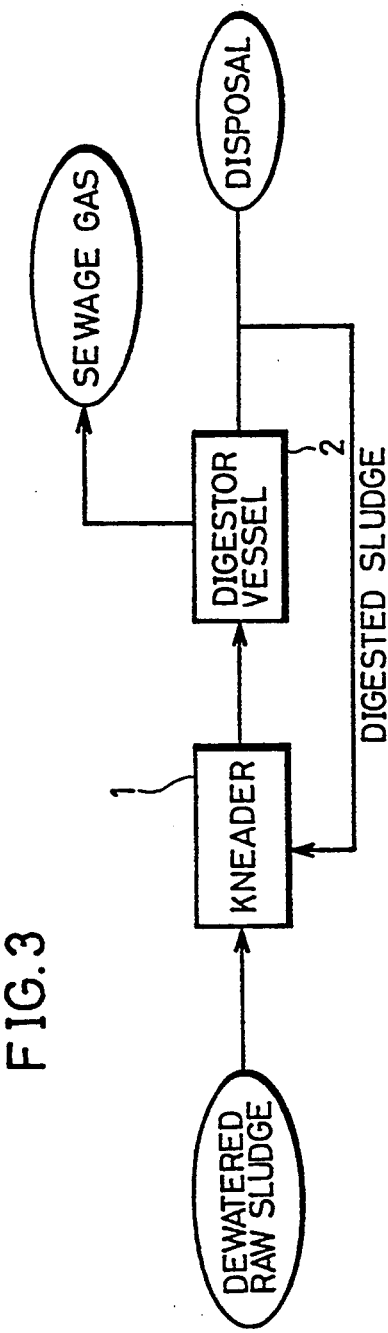
FIG. 3 is a process drawing showing a first embodiment of the present invention.

FIG. 3 is a process drawing showing a first embodiment of the present invention. Referring to FIG. 3, raw sludge dewatered to a solids content of at least 10 weight % is introduced into a kneader 1, to which a portion of the digested sludge is recirculated. The raw sludge is mixed into the digested sludge, serving as seed sludge, in the kneader 1. The kneader 1 is capable of kneading highly viscous substances, and may be a co-kneader, a ribbon mixer or a guillotine mixer, for example. Sludge obtained by kneading the raw sludge with the digested sludge in the kneader 1 is supplied to a digestor chamber 2. In the digestor chamber 2, digestion is performed and sewage gas thus generated is extracted. A great portion of the sludge digested for a predetermined period is fed back to the kneader 1, while the remaining portion is disposed. The large mixing ratio of the digested sludge/raw sludge in the kneader 1 provides stable operation. The preferable weight ratio of digested sludge to dewatered raw sludge, which depends on the efficiency of the kneader, is selected in the range of from 1 to 20.

It is said that methane fermentation is adapted to form methane through two processes of first forming organic acids, alcohols, etc., from organic substances of substrates contained in the sludge, and then forming methane from the organic acids and alcohols. If the ferment bacteria concentration in the raw sludge is low or the raw sludge is heterogeneously mixed with seed sludge and the ferment bacteria concentration is locally reduced, formation of the organic acids and alcohols becomes dominant to inhibit the activity of the methanation bacteria. The rate of methane fermentation depends on the methanation process, and it is said that methanation bacteria are extremely sensitive to the Ph value and the organic acid and alcohol concentration. Therefore, it is necessary to regularly maintain a high concentration of the methanation bacteria in the raw sludge and to mix the raw sludge with the seed sludge so that concentration of the organic acid and alcohol around the methanation bacteria is not in excess of a certain limit. In such mixing of the raw sludge and the seed sludge, it is preferable to increase the initial concentration of the ferment bacteria by increasing the amount of the seed sludge to be circulated, in order to prevent an excessive increase in the concentration of organic acid and alcohol. Thus, equilibrium in a symbiotic relation between the acid forming bacteria and the methanation bacteria is maintained.

Figure 4:
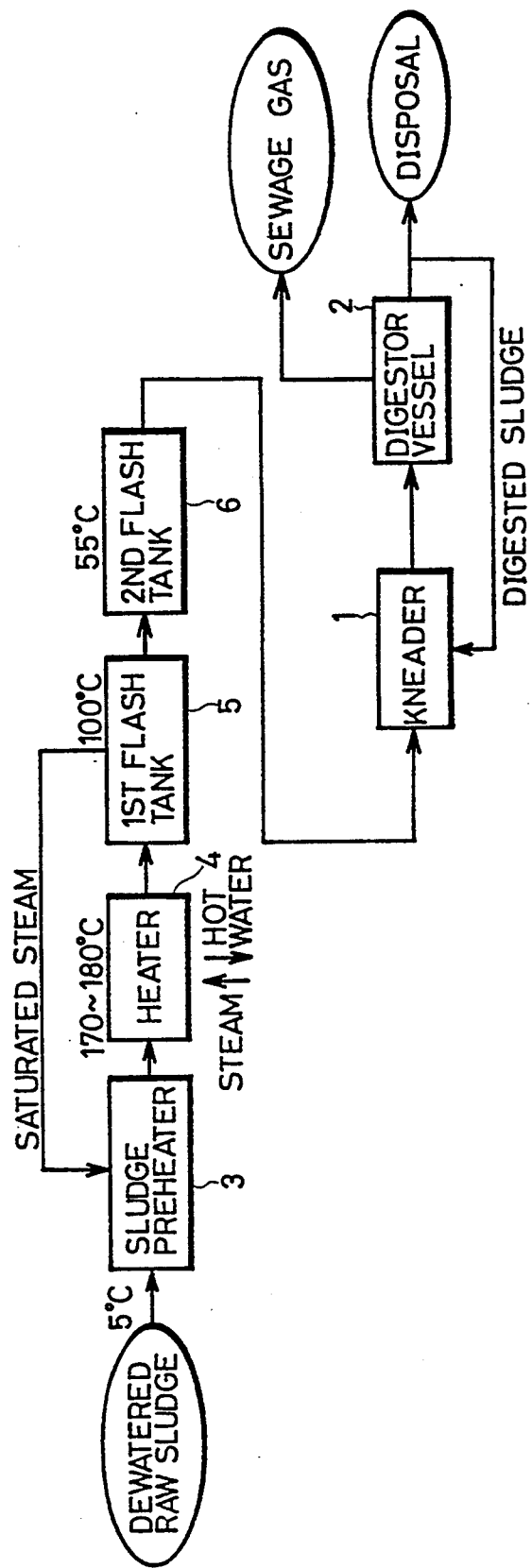
FIG. 4 is a process drawing showing a second embodiment of the present invention.

FIG. 4 is a process drawing showing a second embodiment of the present invention, in which raw sludge is heat-treated before the same is kneaded with seed sludge. Referring to FIG. 4, dewatered raw sludge is supplied to a sludge preheater 3, to be preheated therein. Then the raw sludge is supplied to a heater 4, and heated to a temperature of not less than 50° C., for example, from 60° C. to 180° C. This heater 4 can perform heating with steam, for example. Such steam heating can be made by steam recovered from waste heat of a sewage gas power generation system. The heated sludge is then introduced into a first flash tank 5, and cooled to 100° C. Saturated steam in the first flash tank 5 is fed back to the sludge preheater 1 to heat the raw sludge. Then the raw sludge is introduced into a second flash tank 6 and cooled to 55° C., for example.

The cooled raw sludge is supplied into a kneader 1, and kneaded with a recirculated digested sludge, which serves as seed sludge. The kneaded sludge is fed to a digestor chamber 2, and methane fermentation is conducted at a relatively high temperature of 50° to 55° C., for example. Sewage gas thus generated is extracted from an extracting port, and a large portion of the sludge digested for a predetermined period is fed back to the kneader 1, while the remaining portion is disposed.

Figure 5:
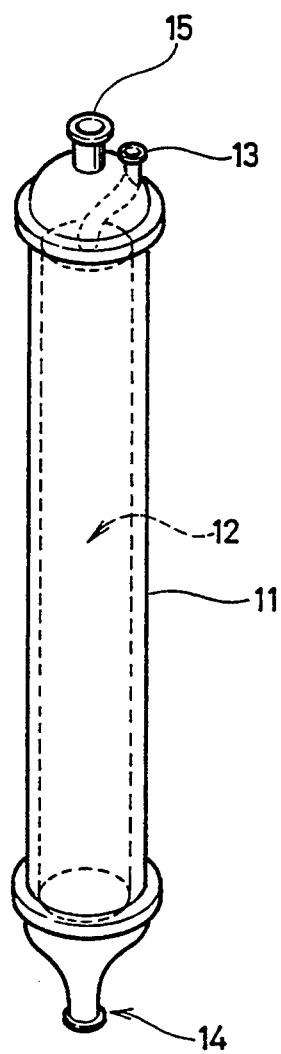
FIG. 5 is a perspective view showing a digestor chamber employed in a bench scale experiment along the process shown in FIG. 4.

The apparatus shown in FIG. 4 was employed to make a bench scale experiment. FIG. 5 shows a tube type digestor chamber employed in this experiment.

Referring to FIG. 5, a tube 12 is provided in a jacket 11. A sludge supply nozzle 13 and a sewage gas exhaust port 15 are provided in an upper end of the tube 12, and a sludge exhaust port 14 is provided in the bottom portion of the jacket 11. Sludge kneaded in the kneader 1 equipped with a heating jacket is supplied to the tube 12 through the sludge supply nozzle 13. The interior of the tube 12 is maintained at a predetermined temperature by the jacket 11. The sludge is digested and downwardly moved in the tube 12. The sludge thus moved in the tube 12 within a constant period is exhausted from the sludge exhaust port 14. Gas generated by such digestion is exhausted from the sewage gas exhaust port 15 provided in the upper portion of the tube 12.

A tube 12, 160 mm in diameter and 3,500 mm in length, was employed and heated by warm water flowing in the jacket 11 so that its interior was at a temperature of 50° to 55° C. The rate for supplying sludge from the sludge supply nozzle 13 was adjusted so that the sludge passed through the tube 12 in one day.

Within the kneader 1 heated to 50° to 55° C., raw sludge (0.84 kg), which was prepared by heat-treating raw sludge of a solids content of 21 weight % at 160° C. for 30 minutes, was kneaded with seed sludge, i.e., digested sludge (12.0 kg). The sludge mixture thus obtained was fed into the tube 12 once every 6 hours intermittently through the sludge supply nozzle 13.

This bench scale test was operated for 15 days to measure the amount of gas generated by digestion and the methane content in the generated gas. As a result, gas was generated at the rate of about 750 l per 1 kg organic substances contained in the raw sludge. The amount of the gas thus generated in this system was considerably larger than that in an ordinary anaerobic digestion process, which is about 500 l per 1 kg organic substances. The methane content was about 60%, which was substantially similar to that in the conventional anaerobic digestion process. It is obvious that the digestion process according to the present invention is excellent also in a bench scale test under conditions further approximate to those for actual operation, since the amount of the generated gas per unit organic substances is significantly improved as compared with that in the conventional digestion process.

Figure 6:
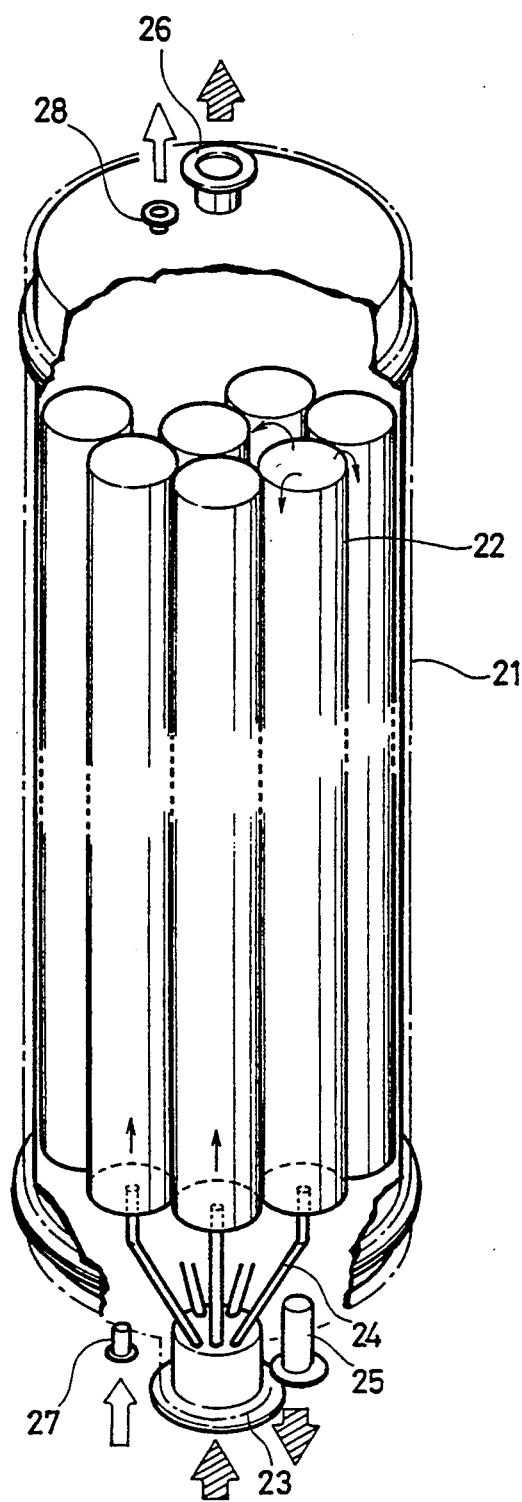
FIG. 6 is a partially fragmented perspective view showing a digestor chamber in the case of applying the present invention to a large scale plant.

FIG. 6 is a partially fragmented perspective view showing an exemplary digestor chamber employed in the case of applying the present invention to a large scale plant. According to the present invention, sludge cannot be digested in a conventional stirring vessel since the sludge has a high viscosity. In one of the effective methods, therefore, the sludge which is kneaded in advance in a kneader is digested during movement in a tube, as shown in FIG. 5. Thus, an apparatus having a plurality of tubes as shown in FIG. 6 can be employed in a large scale plant. Referring to FIG. 6, a plurality of tubes 22 are contained in a jacket 21. The tubes 22 are 0.2 to 1.0 m in diameter and 10 to 30 m in length, for example. The jacket 21 is provided in its bottom portion with a sludge supply port 23, which has sludge distribution nozzles 24 in correspondence with the respective tubes 22. A warm water inlet port 27 and a sludge exhaust port 25 are further provided in the bottom portion of the jacket 21. A sewage gas outlet port 26 for extracting generated gas and a warm water outlet port 28 are provided in an upper portion of the jacket 21.

Sludge supplied from the sludge supply port 23 is pushed into the respective tubes 22 through the sludge distribution nozzles 24. The sludge is gradually upwardly moved within the tubes 22 to overflow the upper ends of the tubes 22, and then downwardly moved along the outer walls of the tubes 22. The sludge thus downwardly moved along the outer walls of the tubes 22 is exhausted from the sludge exhaust port 25, so that a large portion thereof is fed back to the kneader 1 and the remaining portion is disposed.

The sludge is digested during the upward movement within the tubes 22 and the downward movement along the outer walls of the tubes 22. Due to such a system, a long residence time can be ensured even if the tubes 22 are short. Warm water supplied from the warm water inlet port 27 passes through the outer wall of the jacket 21, to be discharged from the warm water outlet port 28. The interior of the jacket 21 is maintained at a predetermined temperature by this warm water.

Through employment of the digestor chamber having a plurality of tubes as shown in FIG. 6, the speed of movement of the sludge within the tubes can be made uniform, thereby to prevent nonuniform movement of the sludge, such as short-circuit flow.

It is to be noted that the digestor chamber shown in FIG. 6 is a mere example of a vessel employable in the present invention, and the present invention is not restricted to the digestor chamber shown in FIG. 6.

Figure 7:
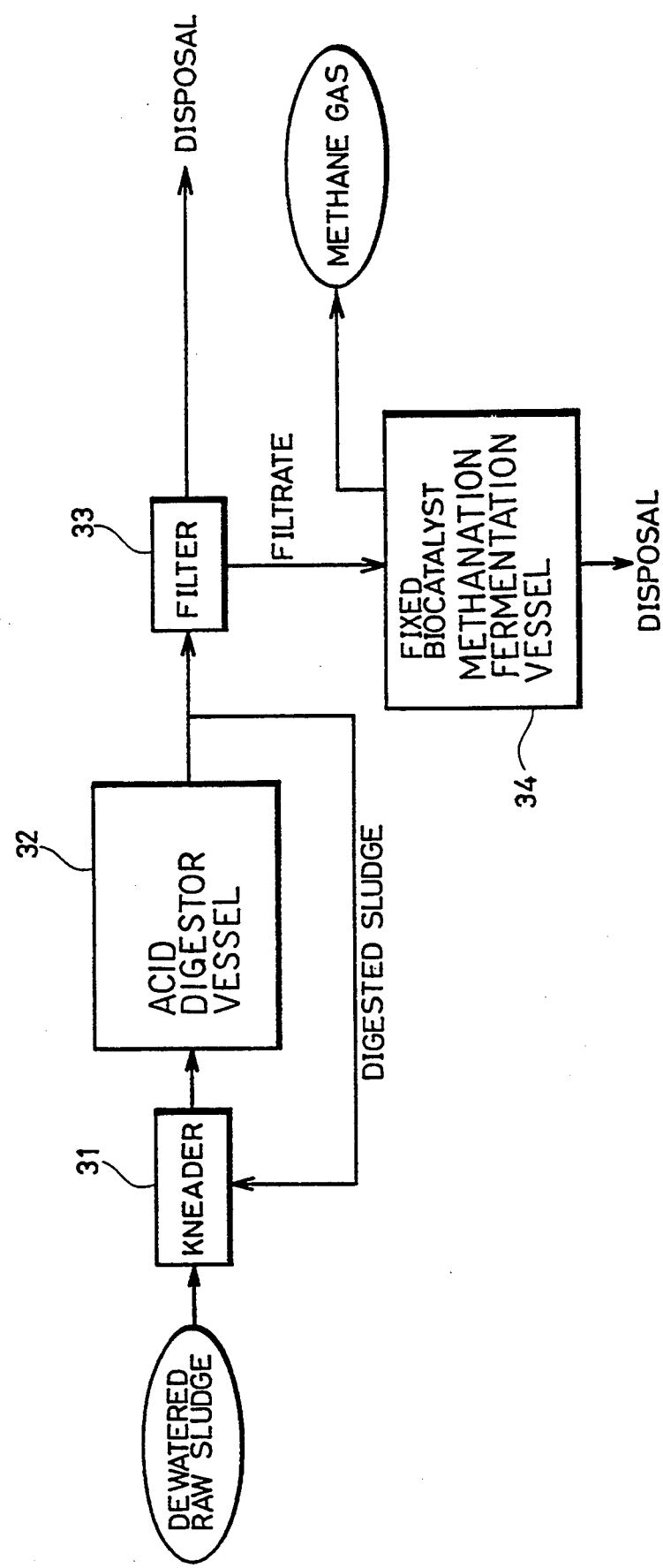
FIG. 7 is a process drawing showing a third embodiment of the present invention.

As hereinabove described, the present invention is also applicable to a two-phase anaerobic digestion process, in which methane fermentation is separated into an acid formation step and a methanation step. FIG. 7 is a process drawing showing an embodiment in which the present invention is applied to such a two-phase anaerobic digestion process. Referring to FIG. 7, dewatered raw sludge is supplied to a kneader 31, to be kneaded with a large portion of digested sludge which is effluent from an acid digester vessel 32. The kneaded sludge is supplied to an acid digestor vessel 32, to be subjected to only an acid formation step. A great portion of the digested sludge after fermentation is fed back to the kneader 31, and the remaining portion is filtered by a filter 33. Organic substances contained in the raw sludge are converted into lower fatty acids, alcohols, carbon dioxide, etc., and solubilized through acid formation fermentation. Thus, such lower fatty acids etc. are dissolved in the filtrate. Solids generated in the filter 33 are disposed. Then the filtrate is supplied to a methanation fermentation vessel 34, in which a biocatalyst for causing methanation fermentation is fixed, to be subjected to methanation fermentation. Biocatalysts for methane fermentation are well known in the art. Methane gas thus generated is extracted and the filtrate passing though the methanation fermentation vessel 34 is disposed. In this embodiment, tube type digestor chambers shown in FIGS. 5 and 6 can be employed as the acid digestor 32.

Furthermore, in this embodiment, raw sludge may be heat-treated in advance before the same is kneaded with seed sludge in a similar manner to the process shown in FIG. 4.

EXAMPLE 3

Digested sludge having a dry solids content of about 1.5 weight % from a thermophilic methane fermentation digestor and raw sewage sludge having the dry solids content of about 4% prior to the methane fermentation were obtained from a sewage treatment plant. The raw sewage sludge was then dewatered by a centrifugal separator, and six different samples of raw sludge, having dry solids contents of 5, 12.0, 16.5, 19.0, 20.5 and 21.5 weight % respectively, were prepared.

In continuous methane fermentation, a dry solids content of digested sludge is lower than that of raw sludge, because a certain amount of organic materials in the raw sludge are digested and converted into gas. An extent of the solids content decrease from raw sludge to digested sludge depends on an organic materials content in raw sludge and a digesting rate. It was considered, however, that in continuous methane fermentation, the raw sludges were digested so that the contents thereof would be changed from 10% to 4–6%, and from 20% to 9–12% respectively. Therefore, in order to provide similar condition to the continuous methane fermentation, the digested sludge having the dry solids content of about 1.5% was dewatered by the centrifugal separator, and six different samples of digested sludge, having dry solids contents of 2.0, 5.0, 7.5, 9.0, 10.0 and 11.0 respectively, were prepared.

Ten weight parts of each digested sludge sample were homogeneously kneaded with one weight part of each corresponding raw sludge sample. By the mixture, were obtained the following six different inoculated sludge samples for the fermentation.

TABLE 1

| | Inoculated Sludge Sample No. | | | | | |
|---|---|---|---|---|---|---|
| | 1 | 2 | 3 | 4 | 5 | 6 |
| Dry Solids Content of Raw Sludge (weight %) | 5.5 | 12.0 | 16.5 | 19.0 | 20.5 | 22.0 |
| Dry Solids Content of Digested Sludge (weight %) | 2.0 | 5.0 | 7.5 | 9.0 | 10.0 | 11.0 |
| Amount for Fermentation (g) | 355.5 | 163.0 | 118.5 | 102.9 | 95.4 | 88.9 |

Figure 8:
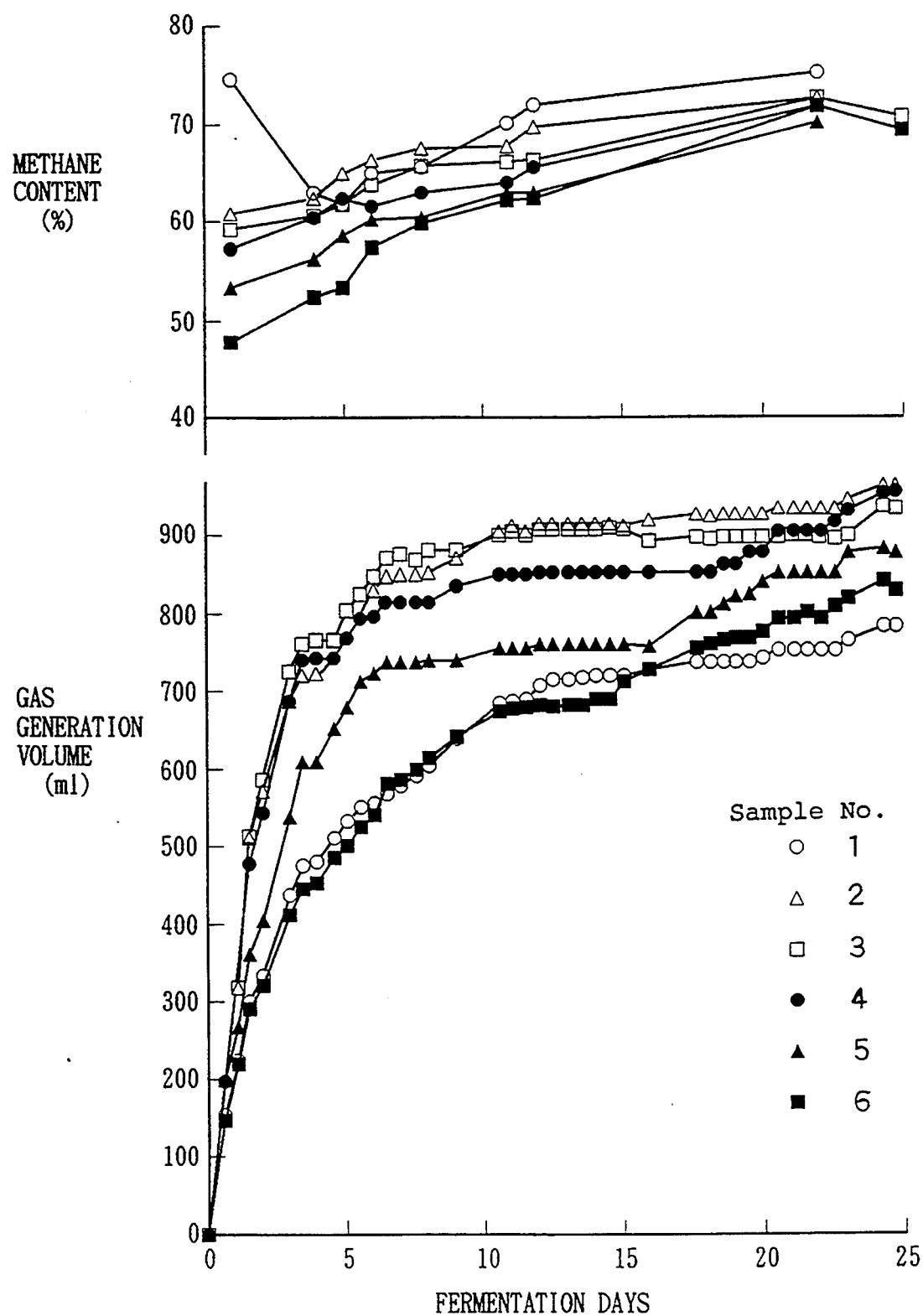
FIG. 8 shows the methane content and gas generation volume as a function of fermentation days for various samples.
Figure 9:
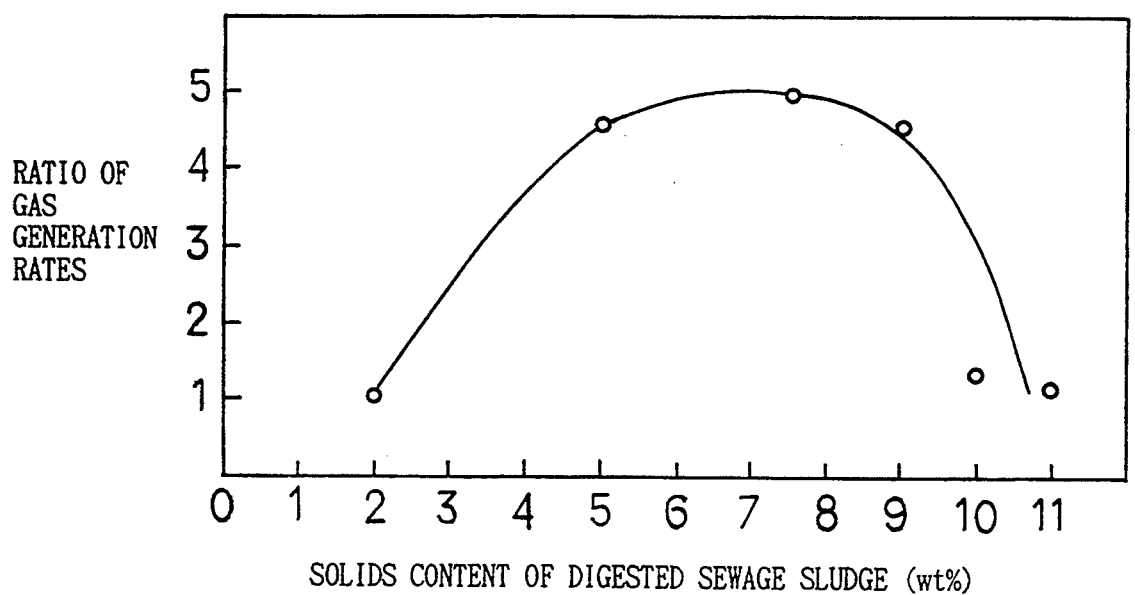
FIG. 9 shows a ratio of gas generation rates as a function of digested sewage sludge solids content.

The amounts of the inoculated sludge samples shown in Table 1 were respectively placed in six tube shaped vessels each having a volume of 500 ml. Each amount for causing the methane fermentation had substantially the same solids amount derived from the raw sludge. The space in the vessel is substituted for nitrogen gas and the opening of the vessel is closed by using a butyl rubber plug having a gas outlet. Each sample in the vessel was incubated in a water bath regulated at 54° C. to cause batch type methane fermentation. FIG. 8 shows the result of experiment. A gas generation rate in each sample was determined by dividing 80% of the maximum gas generation amount by the corresponding time period providing with the 80% of the maximum for each curve shown in FIG. 8. A ratio of the gas generation rate in each sample was then obtained by representing the rate of sample No. 1 as 1. The results are shown in FIG. 9, in which the abscissa shows the dry solids content of the kneaded digested sludge, which is nearly equal to the dry solids content of the inoculated sludge, while the ordinate represents the ratio of gas generation rates.

Figure 10:
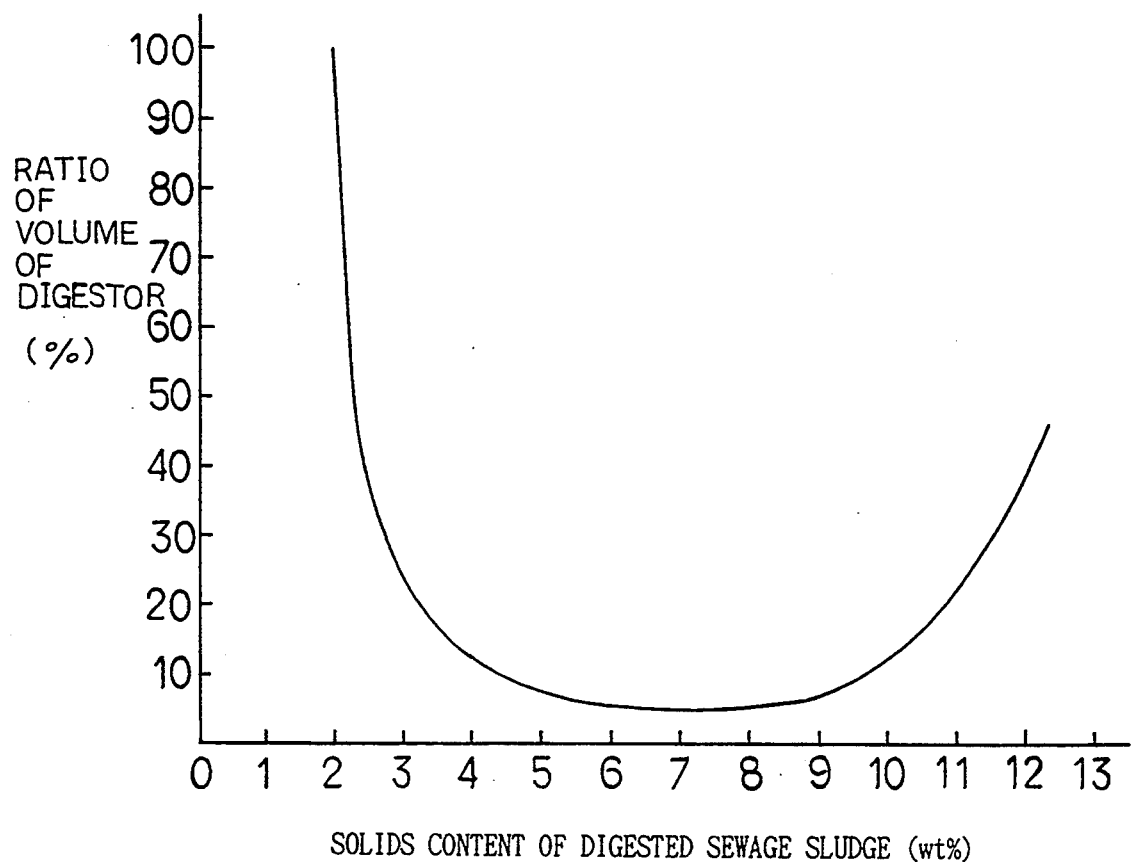
FIG. 10 shows a ratio of digester volume as a function of digested sewage sludge solids content.

In this result of experiment, the rate of gas generation increases as the dry solids content of the sewage sludge increases, and then decreases at 7–8%. The ratio is higher than that of sample No. 1 up to about 11.0% of the solids content. The necessary volume of digestor is in inverse proportion to the gas generation rate and the dry solids content of the inoculated sewage sludge. Based on the result of FIG. 9, the relation between the solids content for methane fermentation and the necessary volume of digestor is shown in FIG. 10. Referring to FIG. 10, the abscissa shows the dry solids content of the digested sewage sludge, which is nearly equal to the dry solids content of the inoculated sewage sludge, and the ordinate represents the ratio of the volume of digestor when the volume for sample No. 1 is represented as 100%. FIG. 10 demonstrates that dry solids contents not less than about 4% by weight are preferred for the digested sludge or the inoculated sludge, and dry solids content in the range of 5–10% by weight is more preferable.

This range is in one example, and general preferred range is in and around the above mentioned. The dry solids content in this range provides with a reduced volume of digestor and a reduced energy necessary for the fermentation.

As hereinabove described, the digestion process according to the present invention is also applicable to the two-phase anaerobic digestion process.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An anaerobic digestion process for sewage sludge, comprising the steps of:

dewatering raw sewage sludge to provide a solids content therein in the range of 10 to 20 weight %;

recirculating a portion of digested sludge resulting from methane fermentation and having a dry solids content lower than that of said dewatered raw sewage sludge and in the range of 4 to 12 weight %;

adding one part by weight of said dewatered raw sewage sludge to at least one part by weight of the recirculated digested sludge;

homogeneously kneading the resulting mixture for inoculation; and causing methane fermentation of the inoculated sludge mixture in a tube-shaped digestor;

said kneading being conducted at a location separate from said digestor, said inoculated sludge being moved in the longitudinal direction of the tube in said digestor without stirring during methane fermentation, and a portion of the sludge discharged from said digestor being recirculated.

2. A process in accordance with claim 1, wherein said raw sewage sludge is heat treated at a temperature in the range of about 60° to about 180° C. prior to addition of the recirculated digested sludge thereto.

3. A process in accordance with claim 1, wherein methane fermentation is effected at a temperature of at least 50° C.

4. A process in accordance with claim 1, wherein said digestor includes a first tube and a second tube covering the first tube, and said sludge mixture is moved upward in said first tube, discharged from said first tube and thereafter moved downward between said first tube and said second tube.

5. A process in accordance with claim 1, wherein the raw sewage sludge has a C/N ratio of 6 to 10.

* * * * *